United States Patent
Srivastava et al.

(10) Patent No.: US 10,413,323 B2
(45) Date of Patent: Sep. 17, 2019

(54) MINIMALLY INVASIVE SURGICAL CANNULA

(71) Applicants: Sudhir Prem Srivastava, Hangzhou (CN); Sugumar Perumalsamy, Madurai (IN)

(72) Inventors: Sudhir Prem Srivastava, Hangzhou (CN); Sugumar Perumalsamy, Madurai (IN)

( * ) Notice: Subject to any disclaimer, the term of this patent is extended or adjusted under 35 U.S.C. 154(b) by 55 days.

(21) Appl. No.: 15/534,987

(22) PCT Filed: Dec. 26, 2014

(86) PCT No.: PCT/IB2014/067348
§ 371 (c)(1),
(2) Date: Jun. 9, 2017

(87) PCT Pub. No.: WO2016/092354
PCT Pub. Date: Jun. 16, 2016

(65) Prior Publication Data
US 2017/0348021 A1     Dec. 7, 2017

(30) Foreign Application Priority Data
Dec. 11, 2014 (IN) .......................... 3650/DEL/2014

(51) Int. Cl.
| A61B 17/34 | (2006.01) |
| --- | --- |
| A61B 17/02 | (2006.01) |
| A61B 17/00 | (2006.01) |
| A61B 34/30 | (2016.01) |
| A61B 90/00 | (2016.01) |

(52) U.S. Cl.
CPC ...... *A61B 17/3421* (2013.01); *A61B 17/0218* (2013.01); *A61B 34/30* (2016.02); *A61B 2017/00477* (2013.01); *A61B 2090/065* (2016.02); *A61B 2090/0808* (2016.02); *A61B 2090/0812* (2016.02)

(58) Field of Classification Search
CPC ............ A61B 1/32; A61B 17/02–0206; A61B 17/025; A61B 17/3421; A61B 17/3423; A61B 17/34; A61B 2017/00477; A61B 2017/0046; A61B 2017/00486
See application file for complete search history.

(56) References Cited

U.S. PATENT DOCUMENTS

| 5,553,198 | A | * | 9/1996 | Wang ..................... A61B 34/70 606/19 |
| --- | --- | --- | --- | --- |
| 5,645,519 | A | * | 7/1997 | Lee ....................... A61B 1/2676 600/114 |
| 5,807,378 | A | * | 9/1998 | Jensen ....................... B25J 3/04 403/316 |

(Continued)

*Primary Examiner* — Eduardo C Robert
*Assistant Examiner* — Michelle C Eckman
(74) *Attorney, Agent, or Firm* — LeClairRyan

(57) ABSTRACT

The present invention is directed to a minimally invasive surgical cannula provided with at least two grooves having a semi-circular profile as a non rotating feature. The non rotating grooves of cannula further accommodates at least one sensor and a strain gauge to detect and measure forces acting on cannula when it is coupled with a modular interfacing arrangement and facilitates maneuvering of surgical instrument inside the body cavity during surgical incision.

9 Claims, 2 Drawing Sheets

(56) References Cited

U.S. PATENT DOCUMENTS

| | | | | |
|---|---|---|---|---|
| 6,132,368 A | * | 10/2000 | Cooper | A61B 46/13 600/102 |
| 2004/0039400 A1 | * | 2/2004 | Schmieding | A61B 17/0281 606/108 |
| 2004/0176763 A1 | * | 9/2004 | Foley | A61B 17/3417 606/60 |
| 2006/0030872 A1 | * | 2/2006 | Culbert | A61B 17/02 606/191 |
| 2006/0161136 A1 | * | 7/2006 | Anderson | A61B 90/57 606/1 |
| 2009/0149857 A1 | * | 6/2009 | Culbert | A61B 1/018 606/80 |
| 2011/0071541 A1 | * | 3/2011 | Prisco | A61B 17/3421 606/130 |
| 2012/0010670 A1 | * | 1/2012 | Pisarnwongs | A61B 17/3421 606/86 R |
| 2012/0296281 A1 | * | 11/2012 | Jaspers | A61B 17/3421 604/164.04 |
| 2013/0079597 A1 | * | 3/2013 | Auerbach | A61B 17/0482 600/204 |
| 2013/0190570 A1 | * | 7/2013 | Hirsch | A61B 17/8861 600/204 |
| 2013/0211423 A1 | * | 8/2013 | Blumenkranz | A61B 17/3462 606/130 |
| 2013/0289354 A1 | * | 10/2013 | Ainsworth | A61B 17/0642 600/204 |
| 2014/0257332 A1 | * | 9/2014 | Zastrozna | A61B 17/1703 606/130 |
| 2016/0270816 A1 | * | 9/2016 | Mather | A61B 17/3423 |
| 2016/0310221 A1 | * | 10/2016 | Bar | A61B 34/30 |
| 2017/0086930 A1 | * | 3/2017 | Thompson | A61B 34/30 |
| 2017/0348021 A1 | * | 12/2017 | Srivastava | A61B 17/3421 |
| 2018/0008313 A1 | * | 1/2018 | Augelli | A61B 17/3423 |
| 2018/0014890 A1 | * | 1/2018 | Stanton | A61B 17/34 |
| 2018/0064461 A1 | * | 3/2018 | Tran | A61B 17/32053 |
| 2018/0161118 A1 | * | 6/2018 | Overmyer | A61B 90/05 |
| 2018/0168671 A1 | * | 6/2018 | Overmyer | A61B 17/295 |
| 2018/0168688 A1 | * | 6/2018 | Schmid | A61B 34/35 |
| 2018/0168689 A1 | * | 6/2018 | Beckman | A61B 34/30 |
| 2018/0168745 A1 | * | 6/2018 | Overmyer | A61B 17/07207 |
| 2018/0168746 A1 | * | 6/2018 | Swayze | A61B 17/3421 |
| 2018/0200013 A1 | * | 7/2018 | Elhawary | A61B 34/30 |
| 2018/0271511 A1 | * | 9/2018 | Stanton | A61B 17/0218 |

\* cited by examiner

MINIMALLY INVASIVE SURGICAL CANNULA

FIELD OF THE INVENTION

The present invention generally relates to minimally invasive-surgical cannula, and more particularly, to a manipulable cannula having parallely arranged anti-rotation grooves.

BACKGROUND OF THE INVENTION

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not just as admissions of prior art.

In the most commonly employed configurations, the coupling mechanism in surgical robotic system transferring the controlling motions from the functional end of the robotic arm to the detachably attached surgical instrument has a finite range of motion owing to the arrangement of components on its either side. The limitation in motion adversely hampers the free movement of the coupling arrangement, so necessitated during the surgery. Now, in order to compensate for the undue loss in free motion of the coupling arrangement, the robotic arm may have to traverse an undesirable broader course that may enhance probability of potential conflict between said arms.

Recently, advancement in coupling mechanism is witnessed in the form of modular interfaces that allow easy detachability of surgical instruments or diagnostic devices and their movement independent of the robotic system during performance of surgery. With introduction of modular interfaces, the traditionally occurring cannula assembly that allows long narrow surgical instruments to work inside the body through small access incision or port site may not be of substantial help owing to the attachment means specific to existing coupling arrangements.

Now, particularly when deploying the interface at the manipulating end of robotic system, since the interface is held freely movable to allow it traverse an undesirable broader course to reach remote aperture sites within the body cavity, the stability of whole interface-cannula complex is of prime concern. Current designs propose various structures, some quiet complex and some not rigid enough to hold cannula intact during full play. In addition, it is desirous to have uniform system of attachment of cannula independent of the size and dimensions of cannula and the connector.

In the light of aforementioned challenges, there exists a need for standard cannula design capable of establishing a rigidifying secure connection with the modular interfacing arrangements and preventing any accidental slippage of cannula during surgery.

SUMMARY OF THE INVENTION

In one general aspect of the invention, a cannula having a proximal and a distal end is provided. The cannula towards its proximal end bears an anti-rotation configuration comprising at least two grooves having a non-circular profile such that a flat surface is defined therebetween closing ends of each groove thereby interrupting an otherwise smooth and continuous circumferential profile of grooved cannula to prevent said cannula from rotating and moving axially when in locked position during surgical insertion.

In one significant aspect of the invention a coupling arrangement including a connector coupling cannula with an interfacing arrangement is provided that comprises a central support member having disposed therewithin a resilient member configured to share an abutting relation with a pair of support member wings extending rearward from the support member towards the interfacing arrangement, said support member further extending in a frontal direction towards the cannula to include at least two pair of gripping members so adapted to securely hold the cannula therebetween and release the cannula, in response to the interaction between the resilient member and the support member wings.

DETAILED DESCRIPTION OF THE INVENTION

Some embodiments of this invention, illustrating all its features, will now be discussed in detail. The following discussion provides many example embodiments of the inventive subject matter. Although each embodiment represents a single combination of inventive elements, the inventive subject matter is considered to include all possible combinations of the disclosed elements.

The invention has for its object an improved cannula attachment system of the aforementioned type that securely attaches to the freely movable modular interfacing arrangement, eliminates possibility of unintended automatic sliding out of cannula so fastened, and is still easy to manufacture and use.

In an advantageous embodiment of the present disclosure, an anti-rotation feature is provided in cannula as it is formed of at least two grooves with a semi-circular profile towards its proximal end. The cannula described herein in the description section of the document is capable of accommodating industry standardized surgical instruments having outside diameters such as 5 mm or 8 mm.

Figure 1:
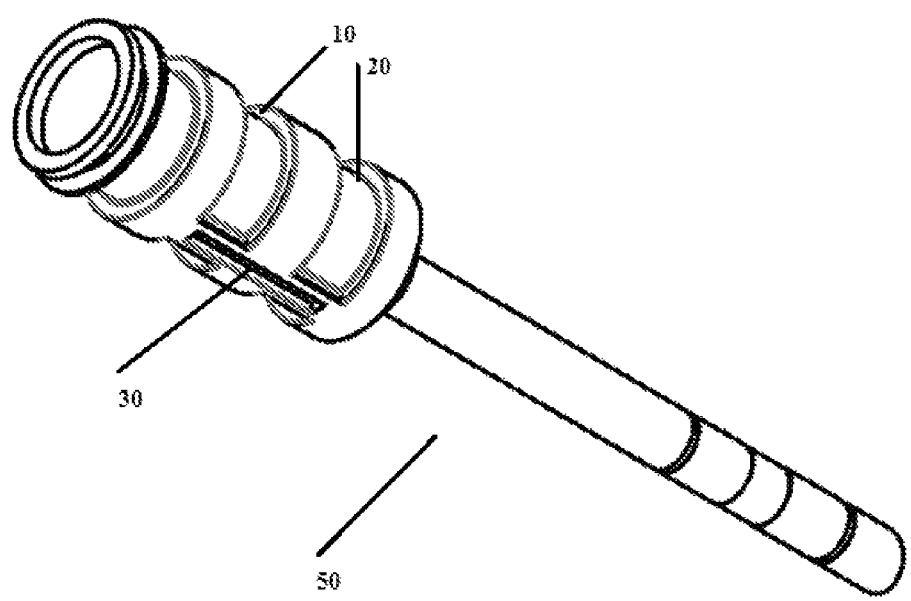
FIG. 1 is a perspective view of cannula in accordance with one general embodiment of the present disclosure

In one general aspect, referring to FIG. 1, a cannula, generally designated by reference numeral 50, with an anti-rotation feature is presented. The figure shows cannula 50 with grooves 10 and 20 that are not rendered fully circular in their profile; rather an intermittent gap is provided in between two closing ends completing the otherwise smooth and continuous circumferential profile of cannula. This serves as a locking mechanism that fixes the cannula 50 at desired angle with respect to the interfacing arrangement 60 and precludes shifting, twisting or any axial movement of cannula 50 once inserted during the surgical incision.

In one another particular embodiment of the present disclosure, the two non-circular grooves 10 & 20, as shown in FIG. 1 defines a plain flat surface extending between the two grooves 10 & 20 that is designed to include a generally longitudinally extending slit 30 therethrough. In the illustrated embodiment, it is to be understood that the slit is provided to pierce only through few inches of cannula wall, approximately ranging between 0.045 to 0.095 inches. The longitudinally extending slit 30 is configured to accommodate therein a sensor and strain gauge (not shown in figure) to detect if the interfacing arrangement 60 is attached securely with the cannula 50, and also to measure forces acting on the cannula 50 by the interfacing arrangement 60 while it is being maneuvered inside the body cavity.

Figure 2:
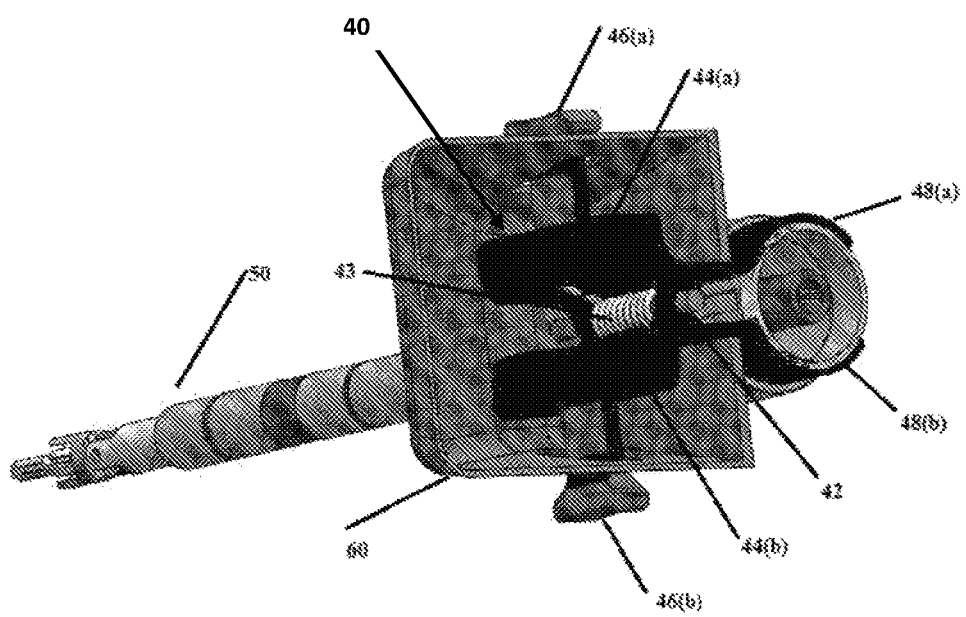
FIG. 2 presents a cross sectional view of an attachment means of cannula in accordance with one other embodiment of the present disclosure.

Now, referring to FIG. 2, a connector 40 configured to attach cannula 50 to the interface arrangement 60 is provided. The connector 40 may include a central support member 42 having disposed therein a resilient member 43 that further shares an abutting relationship with a pair of support member wings 44(a), 44(b) that extends rearward from the support member 42 towards the interfacing arrangement 60. Extending in frontal direction from the central support member 42 towards the cannula are provided at least two pair of gripping members 48(a), 48(b) for engaging the cannula 50 therebetween rigidly and securely to prevent inadvertent slip out during performance of surgery. In one preferred embodiment, the connector 40 may have laterally extending protrusion like clips 46(a), 46(b) that can be pressed inwards to actuate the support member wings 44(a), 44(b) causing compression of resilient member 43 and opening apart of gripping members 48(a) and 48(b).

As can be clearly seen from FIG. 2, the central support member 42 of the connector 40 engageably couples with the tool interfacing arrangement 60 and is configured to receive therewithin a resilient member 43, for example a torsion spring. The resilient member 43 shares an abutting relationship with central support member wings 44(a), 44(b) that are further operably connected with laterally extending protrusions 46(a), 46(b) on either side of the support member 42 such that the protrusions when pressed manually compresses the torsion spring 43, which further causes concomitant movement of gripping members 48(a), 48(b) it is coupled with. Upon compressing the spring 43, the extensions of central support member 42, in the form of grippers 48(a), 48(b) are pulled outwardly of their radial centers so as to receive the cannula 50 therebetween. When released, the torsion spring 43 decompresses to cause the support member wings 44(a), 44(b) to resume their original position, which further causes the two pair of gripping members 48(a), 48(b) to embrace respectively each of the two grooves 10, 20 of the cannula 50 such that the cannula 50 is firmly and rigidly held therebetween the gripping members 48(a) and 48(b).

In one preferred embodiment of the present invention, the sensor and the strain gauge are accommodated at least in part in the slit 30 such that the sensor and the strain gauge protrude outward of the slit 30. Now, as the clips 46(a), 46(b) are pressed inwards, the partially protruding sensor and strain gauge deforms as it presses against the central support member 42, which helps the sensor to detect if the cannula is adequately held by the interface arrangement 60. Likewise in its configuration with respect to the central support member 42, the strain gauge also protruding partially out gets pressed when cannula 50 is held by the interfacing arrangement 60 and measure forces acting on the cannula 50 by the interfacing arrangement 60 when it is maneuvered inside the body cavity.

The foregoing description has been directed to one or more specific embodiments of this invention. It will be apparent; however, that other variations and modifications may be made to the described embodiments, with the attainment of some or all of their advantages. Accordingly this description is to be taken only by way of example and not to otherwise limit the scope of the invention. Therefore, it is the object of the appended claims to cover all such variations and modifications as come within the true spirit and scope of the invention.

What is claimed is:

1. A cannula apparatus for surgical insertion movable between locked and unlocked positions, the cannula apparatus comprising:
   a cannula having proximal end and a distal end;
   a connector to which the cannula is releasably attached, the connector including a central support member, protruding clips, and a pair of gripping members, the central support member including a resilient member disposed therein,
   wherein the proximal end of the cannula has an anti-rotation configuration comprising at least two grooves having closing ends and a non-circular profile, the non-circular profile defining a flat surface between the closing ends of each groove to prevent the cannula from rotating and moving axially when in the locked position during surgical insertion, and
   wherein pressing of the clips inwards causes compression of the resilient member and opening apart of the gripping members to release the cannula.

2. The cannula apparatus of claim 1, wherein the flat surface between the closing end of each groove further defines a slit to accommodate at least in part one sensor to detect if the cannula is securely engaged with a robotic arm.

3. The cannula apparatus of claim 2, wherein the slit is configured to accommodate at least in part a strain gauge to measure force exerted on the cannula by an interfacing arrangement engageable therewith.

4. The cannula apparatus of claim 2, wherein the slit is formed to pierce through a small section of a cannula wall, between 0.045 to 0.095 inches.

5. A coupling arrangement including a connector coupling a cannula with an interfacing arrangement, the connector comprising:
   a central support member having disposed therewithin a resilient member configured to share an abutting relation with a pair of support member wings extending rearward from the central support member towards the interfacing arrangement, the central support member further extending in a frontal direction towards the cannula to include at least a pair of gripping members so adapted to securely hold the cannula therebetween; and
   a protruding clip on either side of the central support member such that pressing of the clip inwards causing compression of the resilient member and opening apart of the pair of gripping members to release the cannula.

6. The coupling arrangement of claim 5, wherein the resilient member is a torsion spring.

7. The coupling arrangement of claim 5, wherein in response to pressing of the support member wings inwards concomitant outward pulling of the pair of gripping members from their radial centers occurs so as to securely receive the cannula therebetween, and in response to releasing of the support member wings, the pair of gripping members overlap to securely and rigidly hold the cannula therewithin.

8. The coupling arrangement of claim 5, wherein the connector connecting the interfacing arrangement with the cannula involves a cannula comprising at least two grooves having a non-circular profile to define a flat surface between closing ends of two grooves, the flat surface further accommodating thereupon a slit to house at least in part one protruding sensor and a strain gauge.

9. The coupling arrangement of claim 5, wherein the pair of gripping members are configured to embrace each respective grooved section of the cannula such that the protruding sensor or the strain gauge housed partially within the slit of cannula presses against the central support member to detect and measure forces acting on the cannula by the interfacing arrangement.

* * * * *